(12) United States Patent
Sensinger et al.

(10) Patent No.: US 12,150,868 B2
(45) Date of Patent: Nov. 26, 2024

(54) SYSTEMS AND METHODS FOR INDUCTIVE TUNING OF HUMAN-MACHINE INTERFACE

(71) Applicant: UNIVERSITY OF NEW BRUNSWICK, Fredericton (CA)

(72) Inventors: Jonathon Sensinger, Fredericton (CA); Kurt Stewart, Västergötland (SE); Anjana Gayathri Arunachalam, Fredericton (CA); Kevin Brian Englehart, Fredericton (CA)

(73) Assignee: UNIVERSITY OF NEW BRUNSWICK, Fredericton (CA)

( * ) Notice: Subject to any disclaimer, the term of this patent is extended or adjusted under 35 U.S.C. 154(b) by 839 days.

(21) Appl. No.: 17/413,305

(22) PCT Filed: Dec. 11, 2019

(86) PCT No.: PCT/CA2019/051786
§ 371 (c)(1),
(2) Date: Jun. 11, 2021

(87) PCT Pub. No.: WO2020/118434
PCT Pub. Date: Jun. 18, 2020

(65) Prior Publication Data
US 2021/0307940 A1    Oct. 7, 2021

Related U.S. Application Data

(60) Provisional application No. 62/778,107, filed on Dec. 11, 2018.

(51) Int. Cl.
*A61F 2/70*    (2006.01)
*A61F 2/68*    (2006.01)
(Continued)

(52) U.S. Cl.
CPC ............... *A61F 2/70* (2013.01); *A61F 2/68* (2013.01); *A61F 2/76* (2013.01); *G06F 3/033* (2013.01);
(Continued)

(58) Field of Classification Search
CPC ................................... G06F 18/214
See application file for complete search history.

(56) References Cited

U.S. PATENT DOCUMENTS 9,465,902 B1    10/2016    Brugada et al.
9,607,387 B2    3/2017    Okuyan et al.
(Continued)

FOREIGN PATENT DOCUMENTS

CA    3040976 A1    4/2018
EP    2770384 A1    8/2014
EP    2863177 A1    4/2015

OTHER PUBLICATIONS

E. A. Clancy, E. L. Morin, and R. Merletti, "Sampling, noise-reduction and amplitude estimation issues in surface electromyography," J. Electromyogr. Kinesiol., vol. 12, pp. 1-16, 2002.
(Continued)

*Primary Examiner* — Gustavo Polo
(74) *Attorney, Agent, or Firm* — HILL & SCHUMACHER

(57) ABSTRACT

Systems and methods are provided for configuring a human-machine interface according to a user's relative preference, or weighting, of a set of utility factors, such that a user can customize a human-machine interface in the absence of the direct selection of interface parameters. In some example embodiments, a total utility function (associated with overall utility of a human-machine interface) is calculated based on the sum of a set of weighted utility functions, with each utility function being weighted according to a respective
(Continued)

user-tunable weight, and with each user-tunable weight prescribing a relative importance of a respective utility factor to the total utility function. A set of parameters of the human-machine interface that optimize the overall utility function for a selected set of user-tunable weights is determined and employed to configure the human-machine interface.

26 Claims, 2 Drawing Sheets

(51) Int. Cl.
    *A61F 2/76*       (2006.01)
    *G06F 3/033*     (2013.01)
    *G06F 18/214*   (2023.01)
    *G06N 3/02*      (2006.01)
    *G06N 3/08*      (2023.01)
    *G16H 40/63*    (2018.01)

(52) U.S. Cl.
    CPC .............. *G06F 18/214* (2023.01); *G06N 3/08* (2013.01); *G16H 40/63* (2018.01); *A61F 2002/6827* (2013.01); *A61F 2002/7635* (2013.01); *A61F 2002/7645* (2013.01); *A61F 2002/769* (2013.01); *G06N 3/02* (2013.01)

(56) References Cited

U.S. PATENT DOCUMENTS

| | | | |
|---|---|---|---|
| 9,676,382 | B2 | 6/2017 | Schwartz et al. |
| 2006/0095855 | A1 | 5/2006 | Britt et al. |
| 2021/0089841 | A1* | 3/2021 | Mithun ..................... G06T 7/90 |

OTHER PUBLICATIONS

E. Todorov and M. I. Jordan, "Optimal feedback control as a theory of motor coordination.," Nat. Neurosci., vol. 5, No. 11, pp. 1226-1235, Nov. 2002.
K. Kording and D. M. Wolpert, "The loss function of sensorimotor learning.," Proc. Natl. Acad. Sci. U. S. A., vol. 101, No. 26, pp. 9839-9842, Jun. 2004.
X. Mu, "Dynamics and motion regulation of a five-link biped robot walking in the sagittal plane," University of Manitoba, 2004. Chapter 2, 162 pages.
E. Todorov, "Optimality principles in sensorimotor control," Nat. Neurosci., vol. 7, No. 9, pp. 907-915, 2004.
E. Todorov, "Stochastic optimal control and estimation methods adapted to the noise characteristics of the sensorimotor system.," Neural Comput., vol. 17, No. 5, pp. 1084-1108, May 2005.
A. Fishbach, S. A. Roy, C. Bastianen, L. E. Miller, and J.C. Houk, "Deciding when and how to correct a movement: Discrete submovements as a decision making process," Exp. Brain Res., vol. 177, No. 1, pp. 45-63, 2007.
E. R. Westervelt, J. W. Grizzle, C. Chevallereau, J. H. Choi, and B. Morris, Feedback Control of Dynamic Bipedal Robot Locomotion. New York, NY: CRC Press, 2007. Chapter 3-6, 521 pages.
M. Berniker and K. Kording, "Estimating the sources of motor errors for adaptation and generalization.," Nat. Neurosci., vol. 11, No. 12, pp. 1454-1461, Dec. 2008.
M. F. Eilenberg, H. Geyer, and H. Herr, "Control of a Powered Ankle-Foot Prosthesis Based on a Neuromuscular Model," Ieee Trans. Neural Syst. Rehabil. Eng., vol. 18, No. 2, pp. 164-173, 2010.
Shadmehr (R. Shadmehr and S. Mussa-Ivaldi, "Biological Learning and Control: How the Brain Builds Representations, Predicts Events, and Makes Decisions", No. August. Cambridge, MA: MIT Press, 2012. Chapters 10-12, 397 pages.
R. D. Gregg, T. Lenzi, L. Hargrove, and J. Sensinger, "Virtual constraint control of a powered prosthetic leg: from simulation to experiments with transfemoral amputees," IEEE Trans. Robot., vol. 30, No. 6, pp. 1455-1471, 2014.
M. McGrath, "Appropriately complex modelling of healthy human walking," University of Salford, 2014. Chapters 3-5, 244 pages.
E. Scheme, B. Lock, and L. Hargrove, "Motion Normalized Proportional Control for Improved Pattern Recognition-Based Myoelectric Control," IEEE Trans. Neural Syst. Rehabil. Eng., vol. 22, No. 1, pp. 149-157, 2014.
J. W. Sensinger, A. Aleman-Zapata, and K. Englehart, "Do cost functions for tracking error generalize across tasks with different noise levels?," PLoS One, vol. 10, No. 8, p. e0136251, 2015.
Gajos, K., Automatically Generating Personalized User Interfaces, PHD Thesis, University of Washington, 2008, 210 pages.
International search report for PCT/CA2019/051786 dated Mar. 23, 2020, 3 pages.

* cited by examiner

SYSTEMS AND METHODS FOR INDUCTIVE TUNING OF HUMAN-MACHINE INTERFACE

CROSS-REFERENCE TO RELATED APPLICATION

This application is a National Phase application claiming the benefit of the international PCT Patent Application No. PCT/CA2019/051786, filed on Dec. 11, 2019, in English, which claims priority to U.S. Provisional Patent Application No. 62/778,107, titled "SYSTEMS AND METHODS FOR INDUCTIVE TUNING OF HUMAN-MACHINE INTERFACE" and filed on Dec. 11, 2018, the entire contents of which is incorporated herein by reference.

BACKGROUND

The present disclosure relates to human-machine interfaces. In some aspects, the present disclosure relates to powered orthoses and prostheses.

Human-machine interfaces enable humans to interface with devices such as computers, vehicles, gaming consoles, powered prostheses and powered orthoses.

SUMMARY

Systems and methods are provided for configuring a human-machine interface according to a user's relative preference, or weighting, of a set of utility factors, such that a user can customize a human-machine interface in the absence of the direct selection of interface parameters. In some example embodiments, a total utility function (associated with overall utility of a human-machine interface) is calculated based on the sum of a set of weighted utility functions, with each utility function being weighted according to a respective user-tunable weight, and with each user-tunable weight prescribing a relative importance of a respective utility factor to the total utility function. A set of parameters of the human-machine interface that optimize the overall utility function for a selected set of user-tunable weights is determined and employed to configure the human-machine interface.

Accordingly, in a first aspect, there is provided a method of configuring a human-machine interface according to utility, the method comprising:
  obtaining a model for a human-machine interface, the model mapping user input to output of a machine, wherein the human-machine interface is customizable according to a plurality of parameters, and wherein the model is dependent on the plurality of parameters;
  determining a total utility function associated with the human-machine interface, wherein the total utility function includes a sum of a plurality of weighted utility functions, each weighted utility function depending on a respective utility factor, wherein each utility factor is associated with the utility of the human-machine interface as perceived by a user, wherein each weighted utility function is weighted according to a respective user-tunable weight, each user-tunable weight prescribing a relative importance of a respective utility factor to the total utility function, wherein the plurality of user-tunable weights associated with the total utility function define a set of user-tunable weights;
  employing the model to determine, for each set of a plurality of different sets of user-tunable weights, a respective set of parameters that produces an optimized total utility function, thereby obtaining a reference dataset associating different sets of user-tunable weights with respective total-utility-optimized parameters of the human-machine interface;
  programming the human-machine interface such that, after receiving input from a user selecting preferred values of the user-tunable weights, the following operations are performed:
    a set of total-utility-optimized parameters are determined, based on the preferred values of the user-tunable weights and the reference dataset, for configuring the human-machine interface; and
    the human-machine interface is configured according to the set of total-utility-optimized parameters, such that the human-machine interface is indirectly configurable according to user input defining the preferred values of the user-tunable weights, in the absence of user input directly prescribing values for the plurality of parameters.

In another aspect, there is provided a method of configuring a human-machine interface according to user-perceived utility preference, the method comprising:
  receiving input from a user selecting preferred values of a set of user-tunable weights for determining a total utility function associated with the human-machine interface, wherein the total utility function includes a sum of a plurality of weighted utility functions, each weighted utility function depending on a respective utility factor, wherein each utility factor is associated with the utility of the human-machine interface as perceived by a user, wherein each weighted utility function is weighted according to a respective user-tunable weight, each user-tunable weight prescribing a relative importance of a respective utility factor to the total utility function, wherein the plurality of user-tunable weights associated with the total utility function define the set of user-tunable weights;
  determining a set of total-utility-optimized parameters based on the preferred values of the user-tunable weights and a reference dataset, the reference dataset providing, for each set of a plurality of different sets of user-tunable weights, a respective set of parameters that produces an optimized total utility function; and
  configuring the human-machine interface according to the set of total-utility-optimized parameters, such that the human-machine interface is indirectly configurable according to user input defining the preferred values of the user-tunable weights, in the absence of user input directly prescribing values for the plurality of parameters.

In another aspect, there is provided a system comprising:
  a human-machine interface; and
  a machine operatively coupled to the human-machine interface;
  the human-machine interface comprising at least one processor and associated memory, wherein the memory stores instructions executable by the at least one processor for performing operations comprising:
    receiving input from a user selecting preferred values of a set of user-tunable weights for determining a total utility function associated with the human-machine interface, wherein the total utility function includes a sum of a plurality of weighted utility functions, each weighted utility function depending on a respective utility factor, wherein each utility factor is associated with the utility of the human-machine interface as perceived by a user, wherein each weighted utility function is weighted according to a respective user-tunable weight, each user-tunable weight prescribing a relative importance of a respective utility factor to the total utility function, wherein the plurality of user-tunable weights associated with the total utility function define the set of user-tunable weights;

determining a set of total-utility-optimized parameters based on the preferred values of the user-tunable weights and a reference dataset, the reference dataset providing, for each set of a plurality of different sets of user-tunable weights, a respective set of parameters that produces an optimized total utility function; and configuring the human-machine interface according to the set of total-utility-optimized parameters, such that the human-machine interface is indirectly configurable according to user input defining the preferred values of the user-tunable weights, in the absence of user input directly prescribing values for the plurality of parameters.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
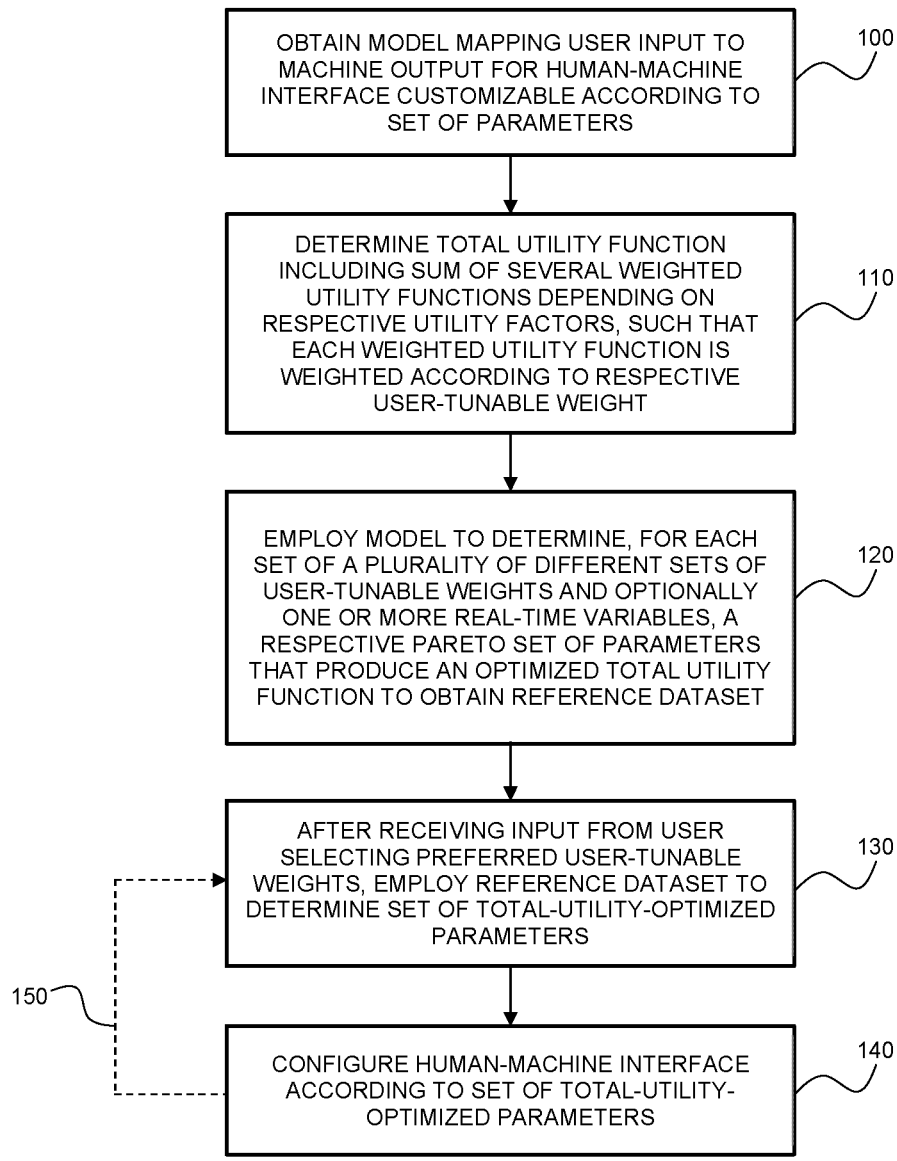
FIG. 1 is a flow chart illustrating an example method of configuring a human-machine interface according to utility preferences of a user.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

A human-machine interface facilitates interaction between a human and a machine. For example, a human-machine interface may be employed to facilitate the transduction of input from a user into input signals and the processing of the input signals to generate control signals suitable for controlling a machine. A human-machine interface can facilitate, for example, the unidirectional or bidirectional transmission of information, forces, and/or motion between a human and a machine. Non-limiting examples of human-machine interfaces include a touchscreen display, computer mouse, joystick, steering wheel, electrode sensing device and pressure sensing interface, and associated processing circuitry for generating suitable control signals. The machine that is controlled by the human-machine interface may be a mechanical machine, such as, but not limited to, a powered prosthesis or a powered orthosis (e.g. an exoskeleton), or non-mechanical machine such as, but not limited to, a computing device, or a combination thereof, such as, but not limited to, a vehicle.

A human-machine interface may facilitate the control of a machine via a mapping relation that prescribes how input signals obtained based on the sensing of input from a human are processed to generate signals for the control of the machine (or more generally, as input to the machine). In the example case of a computer mouse, a position-to-position mapping is typically employed that provides a relationship between sensed motion of the mouse and the control of the display of a cursor. Accordingly, when the mouse is translated to the right, the mouse generates control signals for controlling the display of the cursor, such that the displayed cursor also moves to the right. In contrast, a joystick typically employs a force-to-speed mapping such that when the joystick is actuated to the right, the cursor on the screen moves to the right at a constant speed (when the joystick is actuated to a constant position) until the joystick is released.

In general, a wide range of mappings can be employed to facilitate the control of a controllable device via a human machine interface and in some cases, multiple mappings may be available (e.g. selectable) for controlling a machine based on input from a human. A mapping may be prescribed or defined such that the mapping is dependent on parameters that affect how the input signals are converted into control signals. For example, in the case of the computer mouse, an example parameter is the sensitivity of the mouse.

The parameters associated with a mapping may be customizable (e.g. tunable) by the user. In many cases, tuning these parameters can involve tradeoffs that are perceived by the user as impacting the utility of the human-machine interface for controlling the machine. For example, in the case of a computer mouse, if the mouse sensitivity is tuned to be too high, it can be difficult to achieve accuracy, while if the sensitivity is tuned too low, it can take too long for the cursor to be translated from one side of the screen to the other. In both cases, the user perceives the sub-optimal tuning of the sensitivity as impacting the overall utility of the mouse, which can be understood as adding a utility that reduces the overall utility.

In general, the overall utility of a human-machine interface for the control of a machine may depend on a number of utility factors. In the preceding example involving the computer mouse, changes in the mouse sensitivity (a customizable parameter of the mouse interface) resulted in a perceived utility that reduces overall utility due to a loss of utility associated with the utility factors of accuracy and time.

The utility factors associated with the overall utility of a human-machine interface can vary significantly, for example, among different types of human-machine interfaces, different types of machines, different types of applications and/or different types of users. Examples of utility factors include, but are not limited to, speed, accuracy, effort, energy, force or torque, properties of kinematics (position, speed, acceleration, jerk), consistency (variance), biomimicry (how human-like a movement looks), stability and complexity.

The impact of a given utility factor to the overall utility can be expressed in terms of a utility function that is dependent on the utility factor. For example, a utility function associated with a given utility factor will prescribe whether double the amount produces double the utility, or quadruple the utility, or some other function that maps the factor to the utility. There is extensive behavioural research in psychology, economics, and human movement that shows that almost all utility functions are well-described as quadratic utility, meaning that larger values provide increasingly more utility than smaller values. One exception is temporal discounting, which consistently has a hyperbolic utility-function across various time-scales. It will be understood that the phrase "utility function", as used herein, refers to any function that is dependent on utility and is either maximized or minimized when utility is optimized (maximized). A function that is minimized when overall utility is maximized may be referred to as a "cost function".

Some human-machine interfaces are tuned to provide the best match for an "average user", whereas others enable end-users to directly control interface parameters (such as mouse sensitivity) to their liking for fixed mapping, such as the adjustment of mouse sensitivity. When attempting to configure a human-machine interface via direct adjustment of interface parameters, users often implicitly balance the effect of such utility factors, without even explicitly defining or understanding them. In general, users implicitly care differently about various utility factors and will adjust their selection of interface parameters to customize the human-machine interface accordingly. For example, in the case of the computer mouse, one user may be willing to move their mouse faster, even if this configuration produces less accuracy, whereas another user may place a higher importance on accuracy and be willing to sacrifice speed to achieve it.

Although it may be fairly easy for the user of a computer mouse to vary the tuning parameter of mouse sensitivity in order to achieve a desired overall utility, this ease of tuning and configuration does not generalize to many types of human-machine interfaces. Indeed, many types of human-machine interfaces, such as, for example, human-machine interfaces associated with powered prostheses or powered orthoses, often employ a complex set of interface parameters instead of a single interface parameter, and function such that complex interactions exist between interface parameters and overall utility, with the consequence that it can be too difficult or onerous for a user to accurately adjust the interface parameters in order to find a suitable set of parameter values that optimizes overall utility for the user.

Accordingly, in many types of human-machine interfaces, a significant problem exists in that the user is not readily able to configure the interface for optimal utility via adjustment of the interface parameters. Moreover, since mappings are typically fixed in nature for conventional human-machine interfaces, it is generally not possible for the user to vary the mapping in order to achieve optimal utility.

In order to overcome the problems associated with conventional human-machine interfaces designs, the present inventors sought to provide a human-machine interface that is configurable according to a user's relative preference, or weighting, of a set of utility factors, such that a user can customize a human-machine interface in the absence of the direct selection of interface parameters. The present inventors realized that such customization could be achieved by expressing a total utility function (associated with overall utility of a human-machine interface) as the sum of a set of weighted utility functions, such that each utility function is weighted according to a respective user-tunable weight, with each user-tunable weight prescribing a relative importance of a respective utility factor to the total utility function. As explained below, the parameters underlying the overall utility function may be varied according to criteria associated with the overall utility function (e.g. optimization criteria) in order to customize (e.g. optimize) the human-machine interface according to the selected user-defined weights, instead of being directly tuned by the user. According to such an example method, a human-machine interface may be inductively tuned by a user for the optimization of overall utility via the selection of a set of user-tunable weights without having to explicating tune the parameters of the human-machine interface.

Referring now to FIG. 1, an example method of configuring a human-machine interface is provided, wherein the human-machine interface is customizable according to a set of parameters. As shown in step 100, a model mapping user input to machine output is obtained or provided, where the model is dependent on the parameters of the human-machine interface. Examples of models of human-machine interfaces are provided in detail below.

In step 110, a total utility function is determined for the human-machine interface, wherein the total utility function is based on (i.e. includes at least) the sum of a plurality of weighted utility functions. Each weighted utility function is provided such that it depends on a respective utility factor involving utility that is perceived or perceivable by a user. For example, the total utility function may include at least two weighted utility functions, where one weighted utility function pertains to speed and the other utility function pertains to accuracy. Each utility function is weighted according to a respective user-tunable weight that prescribes the relative importance of its associated respective utility factor to the total utility function. In the example provided above, the speed utility function would be weighted by a speed factor that denotes the relative importance of speed to the overall utility experienced by a given user, and the accuracy utility function would be weighted by an accuracy utility factor that denotes the relative importance of accuracy to the overall utility experienced by a given user. The total utility function is therefore specified by providing a set of user-tunable weights for weighing the various utility functions making up the total utility function. It is noted that examples of determining utility factors for an example human-machine interface are provided below.

In step 120, the model is employed to determine the interface parameters that optimize the overall utility for a wide range of different sets of user-tunable weights. This may be performed, for example, using a global optimization algorithm, such as, but not limited to, genetic algorithms, differential evolution and vulcanization, to find the set of tunable parameters that result in the maximum summed utility function for a given set of weights. It may also be performed using optimal control techniques such as, but not limited to, dynamic programming or Pontryagin's maximum principle; or near-optimal control techniques such as, but not limited to, linear programming, roll-out policies, or model predictive control.

For a given set of user-tunable utility factors, there is typically only a single set of interface parameters that result in optimization. In general, as the user-tunable weights are modified, the interface parameters that optimize overall utility will be different. For example, if a user modifies the user-tunable weights, then suddenly the interface parameters that optimize overall utility will change. The set of optimized interface parameters that respectively correspond to different sets of user-tunable weights may be understood as providing a Pareto set—i.e. the set of interface parameters that correspond to optimizing overall utility across the range of user-tunable weights. When a user selects a given set of user-tunable weights, the Pareto set collapses to a single set of optimal interface parameters. The sets of parameters (e.g. Pareto set of parameters) that are associated with optimized total utility functions for the various sets of user-tunable weights processed in the present step provide a reference dataset that can be employed to generate a suitable set of parameters for an arbitrary set of user-tunable weights. The Pareto set includes the optimum set of parameters across a range of the user tunable weights.

For example, in the present example involving a computer mouse having associated utility factors of speed and accuracy, the interface parameter(s) (e.g. mouse sensitivity and cursor size) that optimize overall utility (maximizes the total utility function) are determined for various different combinations of speed and accuracy utility factor values. In some example embodiments, the model may include one or more real-time variables in addition to the interface parameters (such as, for example, a user-supplied torque), and the Pareto sets of parameters may be determined based on a variety of different values of the real-time variable for each set of user-tunable weights.

When tabulating the reference dataset, the selection of the sets of user-tunable weights may be chosen to obtain a distributed set (e.g. a uniformly distributed set) of Pareto solutions, thereby improving computational efficiency. In one example implementation, this may be performed by determining the sensitivity of the individual utility functions to changes in user-tunable weights relative to a given set of user-tunable weights, and using this sensitivity to select a subsequent set of user-tunable weights.

Having obtained a reference dataset associating the sets of total-utility-optimized parameters with the various sets of user-tunable weights, the human-machine interface may be configured (e.g. programmed) to employ the reference dataset (or a secondary dataset or a relationship obtained by processing the reference dataset) to facilitate the determination of a suitable set of parameters that optimizes the total utility function—thus overall utility—for a given set of user-tunable weights, as shown at 130. For example, the human-machine interface may be programmed to store the reference dataset (or a secondary dataset or another relation derived therefrom) or to access the reference dataset (or a secondary dataset or another relation derived therefrom) from an external data source.

After programming the human-machine interface, user input may be received specifying a set of user-tunable weights corresponding to a user's determination of the prioritization of the utility factors in terms of overall utility. These user-tunable weights may then be employed to determine, from the reference dataset, a suitable set of parameters that optimize the total utility function and thus overall utility.

The reference dataset can be processed in many different ways in order to facilitate the determination of a suitable set of utility-optimized parameters based on a user-selected set of user-tunable weight factors. For example, the reference dataset may be interpolated (e.g. cubic interpolation between optimized data-points), based on the selected user-tunable weights, in order to provide suitable parameters. In an alternative example implementation, the reference data may be processed by training with a neural network. In other example embodiments, the reference dataset can be characterized using a set of Bezier curves or as a closed-form equation. After having determined a suitable set of total-utility-optimized parameters for optimizing the overall utility of the human-machine interface according to user input identifying a selected set of user-tunable weights, the suitable set of parameters may be employed to configure the human-machine interface according to the utility preference of the user, as shown at step 140. Since the reference data is pre-computed, this user-customized utility-optimized configuration of the human-machine interface may be dynamically performed in real-time during use of the machine by a user, or near real-time (e.g. with a short-term lag that is less than a second, or less than 500 milliseconds, or less than 100 milliseconds). In some example implementations, a user may thus repeatedly or continuously configure the human-machine interface by varying the values of one or more of the user-tunable weights, with the human-machine interface responsively and adaptively selecting total-utility-optimized parameter values.

The example method shown in FIG. 1 advantageously facilitates the indirect configuration of a human-machine interface according to the user input defining the preferred values of the user-tunable weights, in the absence of user input directly prescribing values for the set of parameters. In some example embodiments, the mapping that is employed by the human-machine interface may also be configured based on the optimization of the total utility function. For example, a human-machine interface may be customizable according to a plurality of mappings, with each mapping having a respective set of parameters associated therewith, with a plurality of models employing different mappings of user input to machine output. In such a case, step 120 may be performed to determine, for each set of user-tunable weights, the total-utility-optimized mapping that provides an optimal total utility function and the total-utility-optimized parameters associated with the total-utility-optimized mapping. Furthermore, when employing the reference dataset to configure the human-machine interface according to a set of user-tunable weights, the set of total-utility-optimized parameters for configuring the human-machine interface are selected to pertain to the total-utility-optimized mapping.

The present example method described in FIG. 1 advantageously satisfies a user's preference to optimize the human-machine interface according to multiple utility functions associated with multiple utility factors, enabling the configuration of the human-machine interface on an individual basis, or even a task-by-task basis, to adjust the weighing of the utility functions for the optimization of total utility. The present example method thus provides more personalized interfaces between humans and devices based on the utility factors of which humans are actually concerned—as opposed to specific parameters of the human-machine interface, thereby addressing the aforementioned problems with configuring conventional interfaces that only permit parameter adjustment by a user. As noted above, the present example embodiment employs (i) a user's implicit utility-functions, and (ii) a model of the interaction between the user and the device (including, for example, human cognition and device dynamics). Research over the last 50 years, and notably over the last decade, in human-movement, has facilitated the prescription of both of these aspects of the method.

Accordingly, unlike conventional solutions that focus on the optimization of parameters associated with a single utility function, the methods provided according to the present disclosure allow the user to customize (e.g. optimize) the human-machine interface based on the adjustment of user-defined weights that are respectively associated with a plurality of utility functions. As explained above, both the mapping of the human-machine interface and the tuning parameters may be optimized according to the user-tunable weights. The dependence of the mappings and tuning parameters may be pre-determined (e.g. and stored as look-up tables) so that the human-machine interface can be dynamically optimized according to varying user-defined weights. It will be understood that lookup tables, or other data structures or relationships through which the reference data is employed to generate total-utility-optimized parameter sets based user-defined weights, can be machine specific, application specific, and/or user specific.

The example methods described above employ a model to map user inputs to device outputs. Such models may incorporate feedback as the user reacts to the device output. It will be understood that the particular model employed may depend on the type of human-machine interface, the type of machine, and/or the type of task/application. Examples of the application of the example method shown in FIG. 1 to two example prosthetic human-machine interfaces are described in the examples below.

Figure 2:
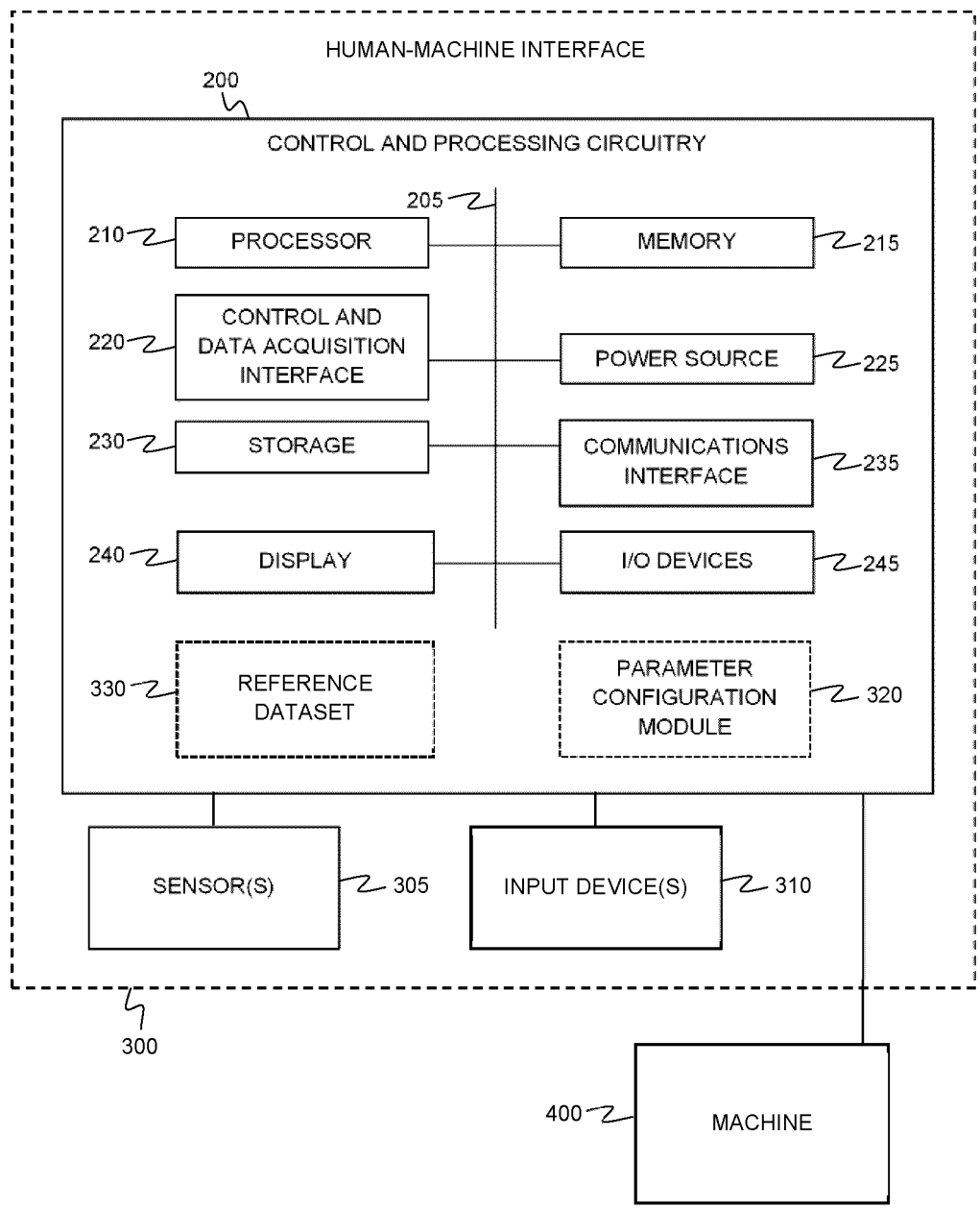
FIG. 2 schematically illustrates a system including a human-machine interface that is configurable according to utility preferences of a user.

Referring now to FIG. 2, an example system is shown that includes a machine 400 (e.g. a powered prosthesis or powered orthosis) that is controllable via, and operatively coupled to, a human-machine interface 300. The human-machine interface 300 includes control and processing circuitry 200. Although not shown in the figure, the machine 400 may include separate control and processing circuitry, including components such as those shown in circuitry 200, which may be operatively connected to one or more mechanical or non-mechanical output components of the machine 400 (such as one or more motors or actuators).

The example human-machine interface 300 includes one or more sensors 305 for sensing signals from a user for the control of the machine (or for providing input to the machine). Nonlimiting examples of such sensors include input devices such as pressure sensors, electrical contact sensors, torque sensors, force sensors, position sensors, current sensors, velocity sensors, and myoelectric sensors. The example human-machine interface 300 also includes one or more input devices 310 for receiving input from a user for selecting the user-tunable weights. Nonlimiting examples of such input devices include joysticks, tuning knobs or sliders, and touchscreen displays (e.g. displays of a mobile computing device).

Although the sensor(s) 305 are shown in the figure as being a component or subcomponent of the human-machine interface 300, in other example implementations, one or more sensors for receiving human input may be external sensors (e.g. sensors residing on or within the machine 400), to which the human-machine interface 300 is interfaced for sensing input. Similarly, the input device(s) 310 may optionally reside external to the human-machine interface 300 while being interfaced thereto.

As shown in the example embodiment illustrated in FIG. 2, control and processing circuitry 200 may include a processor 210, a memory 215, a system bus 205, a data acquisition and control interface 220 for acquiring sensor data and user input and for sending control commands to the machine 400, a power source 225, and a plurality of optional additional devices or components such as storage device 230, communications interface 235, display 240, and one or more input/output devices 245.

The methods described herein can be partially implemented via hardware logic in processor 210 and partially using the instructions stored in memory 215. Some embodiments may be implemented using processor 210 without additional instructions stored in memory 215. Some embodiments are implemented using the instructions stored in memory 215 for execution by one or more microprocessors. For example, the example methods described herein for configuring a human-machine interface according to optimized utility based on user-tunable weights can be implemented via processor 210 and/or memory 215. As shown in FIG. 2, the processing of user-tunable weights, and optionally real-time signals, in order to determine total-utility-optimized parameters for configuring the human-machine interface, is performed via parameter configuration module 320, which employs (directly or indirectly) the reference dataset 330 (which may be stored or externally accessed via the control and processing circuitry 200).

It is to be understood that the example system shown in the figure is not intended to be limited to the components that may be employed in a given implementation. For example, in one example implementation, the processing circuitry 200 may be provided on a computing device that is mechanically supported by the machine 400. Alternatively, one or more components of the processing circuitry 200 may be physically separate from the machine 400. For example, the processing and computing circuitry 200 may include a mobile computing device, such as a tablet or smartphone that is connected to a local processing hardware supported by the machine 400 via one or more wired or wireless connections. In another example implementation, a portion of the control and processing circuitry 400 may be implemented, at least in part, on a remote computing system that connects to a local processing hardware via a remote network, such that some aspects of the processing are performed remotely (e.g. in the cloud).

Although only one of each component is illustrated in FIG. 2, any number of each component can be included. For example, a computer typically contains a number of different data storage media. Furthermore, although the bus 210 is depicted as a single connection between all of the components, it will be appreciated that the bus 210 may represent one or more circuits, devices or communication channels which link two or more of the components. For example, in many computers, bus 210 often includes or is a motherboard.

Although some example embodiments of the present disclosure can be implemented in fully functioning computers and computer systems, various embodiments are capable of being distributed as a computing product in a variety of forms and are capable of being applied regardless of the particular type of machine or computer readable media used to actually effect the distribution.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

As explained above, example embodiments of the present disclosure facilitate the user-specific and utility-optimized configuration of a human-machine interface according to user-tunable weights that are respectively associated with a plurality of utility functions, each utility function characterizing the utility associated with a given utility factor-such that the configuration of the human-machine interface is made based on utility factors without requiring the user to directly tune parameters of the human-machine interface. Indeed, by algorithmically determining the best mapping and parameter values to satisfy a user's utility preference, the approach finds optimal solutions in spaces humans never even would have considered, enabling significantly better performance.

There are a variety of known algorithms that simplify tuning of a human-machine interface, for example, reducing the number of tunable parameters from 50 to two. Unlike the present example embodiments, however, these algorithms assume a fixed and implicit single utility function. An example of such a conventional tuning method is based on virtual constraints (e.g. R. D. Gregg, T. Lenzi, L. Hargrove, and J. Sensinger, "Virtual constraint control of a powered prosthetic leg: from simulation to experiments with transfemoral amputees," IEEE Trans. Robot., vol. 30, no. 6, pp. 1455-1471, 2014). Other examples of algorithms that automate tuning by finding the best parameters for a given single fixed utility-function include BioM's tuning (M. F. Eilenberg, H. Geyer, and H. Herr, "Control of a Powered Ankle-Foot Prosthesis Based on a Neuromuscular Model," Ieee Trans. Neural Syst. Rehabil. Eng., vol. 18, no. 2, pp. 164-173, 2010) and the method of Grizzle's which minimizes energy consumption (E. R. Westervelt, J. W. Grizzle, C. Chevallereau, J. H. Choi, and B. Morris, Feedback Control of Dynamic Bipedal Robot Locomotion. New York, NY: CRC Press, 2007).

EXAMPLES

The following examples are presented to enable those skilled in the art to understand and to practice embodiments of the present disclosure. They should not be considered as a limitation on the scope of the disclosure, but merely as being illustrative and representative thereof.

Configuring Human-Machine Interfaces for Upper and Lower Limb Prosthetic Devices The present example illustrates the application of the method of FIG. 1, in a series of steps, for the configuration of two example human-machine interfaces: H-M Interface A, a human-machine interface providing assistive control of a lower-limb exoskeleton, used by someone with limited leg mobility (such as spinal cord injury or stroke) and H-M Interface B, an upper-limb prosthetic control filter, used by someone controlling a robotic prosthesis with myoelectric control signals.

Step 1: Develop a Model of the Human-Machine Dynamics and Interaction.

H-M Interface 1. A model of walking is derived using Lagrangian dynamics. A control structure of virtual constraints is employed (e.g., according to the example provided by Grizzle; E. R. Westervelt, J. W. Grizzle, C. Chevallereau, J. H. Choi, and B. Morris, Feedback Control of Dynamic Bipedal Robot Locomotion. New York, NY: CRC Press, 2007), which reduces the complex set of dynamics down to a single one-dimensional set of dynamics coupled to a kinematically linked set of joints.

A Lagrangian bipedal model of gait is used that uses ankle-torques rather than feet and that uses an offset trunk mass rather than a trunk linkage to avoid a tree structure. The kinematic location of all of the other joints are linked to the set of dynamics through a phase variable. The relationship between the phase variable and the kinematic position of the other joints is defined by a tunable Bezier curve.

H-M Interface B. Based on the literature, the general model chosen to represent how people behave is a stochastic optimal feedback control model. This model optimizes the expected reward in light of uncertain (stochastic) dynamics.

A stochastic optimal feedback control model is employed with multiplicative noise developed by Todorov (E. Todorov, "Stochastic optimal control and estimation methods adapted to the noise characteristics of the sensorimotor system.," Neural Comput., vol. 17, no. 5, pp. 1084-108, May 2005) and modified by Shadmehr (R. Shadmehr and S. Mussa-Ivaldi, Biological Learning and Control: How the Brain, no. August. Cambridge, MA: MIT Press, 2012) to incorporate the utility of time. The model of the user is able to learn how the device works over time using one of several learning algorithms. The model generates an optimal control policy, and then uses feedback to generate the optimal control signal given the best estimate of the user's current state. The policy is revised if the movement starts to go differently than expected. This model well describes the motor control strategies and behavioural decisions of humans. The model includes a map between the user's control signals (myoelectric control, modeled as having both multiplicative and additive noise).

This model is generated as follows.
1) An estimated model of the task dynamics, along with a utility function (see step 2), are provided to a policy-generation function. This policy generation function iterates, for various fixed times, what the optimal control and feedback gains are, until it has found the optimum task time along with the control and feedback gains for each step of time. This model can handle multiplicative noise in the dynamics and sensors (model developed by Emo Todorov).
2) Based on feedback from sensors, control signals are calculated.
3) Control signals are fed to the true model of the plant dynamics, resulting in motion.
4) This motion is observed, with some sensory delay.
5) The motion is fed back to step 2, where the control policy calculates the next control signals.
6) The motion is also fed back to step 1. If sufficient error exists that it is statistically no longer 0, then the policy is recalculated with a new updated time.

7) The control signals and observations are fed to a model-learning algorithm, which updates the estimated model of the dynamics.
8) Steps 1-7 are iterated until convergence.
9) The total utility of achieving the task can then be calculated.

Step 2: Develop a Utility Function

H-M Interface A. The example utility functions for this interface involve quadratic functions of comfort, effort, speed and biomimicry. Each of these is summed per step. Comfort is defined as the difference between user-supplied torque and exoskeleton supplied torque. Effort is defined as the sum of the torque*speed of the user. Both of these can be calculated as long as the total torque and exoskeleton supplied torque are known. Biomimicry is defined as the deviation from average-gait models. Each of these functions is multiplied by a scalar coefficient to indicate the relative weighting that each is given in the total utility function.

H-M Interface B. The example utility functions for this interface involve quadratic functions of effort, error, and variance. It also involves a hyperbolic function of time. Each of these functions is multiplied by a scalar coefficient to indicate the relative weighting that each is given in the total utility function.

Step 3: Develop a Pareto Set of the Best Tunable Parameters for a Given Set of Values and Real-Time Variables.

H-M Interface A. Tunable parameters include the coefficients of the Bezier curves that are used to enforce the virtual constraints. Real-time variables include the user-supplied torque. The phase variable is a continuous variable. The user-supplied torque is a discrete variable (calculated one per step).

For a given set of utility coefficients (e.g., comfort, effort, etc.) and for a given user-supplied torque, a global optimization is performed to find the best set of tunable parameters, subject to the constraint that the gait remains stable. A Pareto set is then generated that contains the given parameters for a particular set of user-tunable weights (e.g. utility coefficients) and user-supplied torque.

H-M Interface B. Tunable parameters include parameters within the virtual dynamics of the prosthetic arm. These virtual dynamics map how the user's control signal dynamically maps to the motion of the arm. In our preliminary examples, we have a variety of state variables (for example, position, velocity, acceleration, jerk). The mapping between these states and the resultant force is a summed function that includes two tunable parameters per state: a tunable coefficient in front, raised to a tunable power. For example, $$F = a_1 x^{b_1} + a_2 \dot{x}^{b_2} + a_3 \ddot{x}^{b_3} + a_4 \dddot{x}^{b_4},$$

where [a] is the series of tunable coefficients in front and [b] is the series of tunable powers. For a given set of user-tunable weights (utility coefficients; e.g. associated with effort, error, time, etc.), a global optimization is performed to find the best set of tuneable parameters. A Pareto set is then generated that contains the given parameters for a particular set of utility coefficients.

Step 4: Have the User Determine their Particular Set of Values

The user uses a software interface (such as an app), or a physical set of knobs, to tune their desired values for each utility function.

H-M Interface A. The user tunes one knob to tune the relative importance of comfort, one to tune the relative importance of biomimicry, and one to tune the relative importance of effort. From these three relative knobs the relative weight of the four utilities (comfort, effort, biomimicry, and speed) can be determined. A fourth knob determines the desired speed (ranging from slow to fast).

H-M Interface B. The user would tune one knob for effort. Setting this low would require them to generate less effort to achieve the task; setting it high would require them to generate more effort. Another knob would be tuned for accuracy, where a low setting would not guarantee good accuracy, while a high setting would provide high accuracy. The user would tune another knob for variance, which is essentially consistency. Finally, the user would tune another knob for time (how much they cared about completing the task quickly).

Step 5: Run the System.

H-M Interface A. Bezier curves are looked up, given the user's utility values. These then enforce a given set of virtual constraints, which have the person walk. At each step the user-supplied torque is calculated from the previous step, and the Bezier curves are adjusted based on the Pareto set.

H-M Interface B. Given the utility coefficients determined by the user in Step 4, a lookup table would determine the controllable parameters from the Pareto set and apply them to the system. The user would then use the device.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of configuring a human-machine interface according to utility, the method comprising:

obtaining a model for a human-machine interface, the model mapping user input to output of a machine, wherein the human-machine interface is customizable according to a plurality of parameters, and wherein the model is dependent on the plurality of parameters;

determining a total utility function associated with the human-machine interface, wherein the total utility function includes a sum of a plurality of weighted utility functions, each weighted utility function depending on a respective utility factor, wherein each utility factor is associated with the utility of the human-machine interface as perceived by a user, wherein each weighted utility function is weighted according to a respective user-tunable weight, each user-tunable weight prescribing a relative importance of a respective utility factor to the total utility function, wherein the plurality of user-tunable weights associated with the total utility function define a set of user-tunable weights;

employing the model to determine, for each set of a plurality of different sets of user-tunable weights, a respective set of parameters that produces an optimized total utility function, thereby obtaining a reference dataset associating different sets of user-tunable weights with respective total-utility-optimized parameters of the human-machine interface;

programming the human-machine interface such that, after receiving input from a user selecting preferred values of the user-tunable weights, the following operations are performed:
- a set of total-utility-optimized parameters are determined, based on the preferred values of the user-tunable weights and the reference dataset, for configuring the human-machine interface; and
- the human-machine interface is configured according to the set of total-utility-optimized parameters, such that the human-machine interface is indirectly configurable according to user input defining the preferred values of the user-tunable weights, in the absence of user input directly prescribing values for the plurality of parameters.

2. The method according to claim 1 wherein the model includes a real-time variable in addition to the plurality of parameters, wherein the sets of parameters are determined based on a variety of different values of the real-time variable for each set of user-tunable weights.

3. The method according to claim 1 wherein the human-machine interface is further configurable according to a plurality of mappings, each mapping having a respective set of parameters associated therewith, wherein the model is a plurality of models, each model of the plurality of models defining a respective mapping between user input and device output;
- wherein the set of models is further employed to determine, for each set of the plurality of different sets of user-tunable weights, the mapping that provides an optimal total utility function; and
- wherein the set of total-utility-optimized parameters for configuring the human-machine interface pertains to a total-utility-optimized mapping that is also selected according to the preferred values of the user-tunable weights and the reference dataset.

4. The method according to claim 1 wherein the human-machine interface is configured for control of a powered orthosis or a powered prosthesis.

5. The method according to claim 1 wherein the reference dataset is a lookup table.

6. The method according to claim 1 wherein the reference dataset is employed to train a neural network, and wherein the neural network is employed when determining the set of total-utility-optimized parameters.

7. The method according to claim 1 wherein the human-machine interface is programmed such that the set of total-utility-optimized parameters are dynamically determined, in real-time or near-real-time, during use of the machine by a user.

8. The method according to claim 1 wherein the utility factors are selected from the group consisting of a speed measure, an accuracy measure, an effort measure, an energy measure, a force measure, a torque measure, a kinematical measure, a consistency measure, a biomimicry measure, a stability measure and a complexity measure.

9. The method according to claim 1 wherein the human-machine interface is programmed such that the set of total-utility-optimized parameters is specific to one or more of the machine, an application, and the user.

10. The method according to claim 1 wherein the sets of user-tunable weights of the reference dataset are uniformly distributed.

11. The method according to claim 1 wherein the sets of user-tunable weights of the reference dataset are selected according to a sensitivity of the utility function to changes in the user-tunable weights.

12. The method according to claim 1 wherein the model is employed to determine the respective set of parameters that produces an optimized total utility function using an optimal control technique.

13. The method according to claim 12 wherein the optimal control technique employs dynamic programming or Pontryagin's maximum principle.

14. The method according to claim 1 wherein the model is employed to determine the respective set of parameters that produces an optimized total utility function using a near-optimal control technique.

15. The method according to claim 14 wherein the near-optimal control technique is selected from the group consisting of linear programming, roll-out policies, and model predictive control.

16. A method of configuring a human-machine interface according to user-perceived utility preference, the method comprising:
- receiving input from a user selecting preferred values of a set of user-tunable weights for determining a total utility function associated with the human-machine interface, wherein the total utility function includes a sum of a plurality of weighted utility functions, each weighted utility function depending on a respective utility factor, wherein each utility factor is associated with the utility of the human-machine interface as perceived by a user, wherein each weighted utility function is weighted according to a respective user-tunable weight, each user-tunable weight prescribing a relative importance of a respective utility factor to the total utility function, wherein the plurality of user-tunable weights associated with the total utility function define the set of user-tunable weights;
- determining a set of total-utility-optimized parameters based on the preferred values of the user-tunable weights and a reference dataset, the reference dataset providing, for each set of a plurality of different sets of user-tunable weights, a respective set of parameters that produces an optimized total utility function; and
- configuring the human-machine interface according to the set of total-utility-optimized parameters, such that the human-machine interface is indirectly configurable according to user input defining the preferred values of the user-tunable weights, in the absence of user input directly prescribing values for the plurality of parameters.

17. The method according to claim 16 wherein the reference dataset is determined by:
- obtaining a model for a human-machine interface, the model mapping user input to output of a machine, wherein the human-machine interface is customizable according to a plurality of parameters, and wherein the model is dependent on the plurality of parameters; and
- employing the model to determine, for each set of a plurality of different sets of user-tunable weights, the respective set of parameters that produces the optimized total utility function, thereby obtaining the reference dataset.

18. The method according to claim 17 wherein the model includes a real-time variable in addition to the plurality of parameters, wherein the sets of parameters are determined based on a variety of different values of the real-time variable for each set of user-tunable weights.

19. The method according to claim 17 wherein the human-machine interface is further configurable according to a plurality of mappings, each mapping having a respective set of parameters associated therewith, wherein the model is a plurality of models, each model of the plurality of models defining a respective mapping between user input and device output;
    wherein the set of models is further employed to determine, for each set of the plurality of different sets of user-tunable weights, the mapping that provides an optimal total utility function; and
    wherein the set of total-utility-optimized parameters for configuring the human-machine interface pertains to a total-utility-optimized mapping that is also selected according to the preferred values of the user-tunable weights and the reference dataset.

20. The method according to claim 1 wherein the human-machine interface is configured for control of a powered orthosis or a powered prosthesis.

21. The method according to claim 1 wherein the reference dataset is a lookup table.

22. The method according to claim 1 wherein the reference dataset is employed to train a neural network, and wherein the neural network is employed when determining the set of total-utility-optimized parameters.

23. The method according to claim 1 wherein the human-machine interface configured such that the set of total-utility-optimized parameters are dynamically determined, in real-time or near-real-time, during use of the machine by a user.

24. The method according to claim 1 wherein the utility factors are selected from the group consisting of a speed measure, an accuracy measure, an effort measure, an energy measure, a force measure, a torque measure, a kinematical measure, a consistency measure, a biomimicry measure, a stability measure and a complexity measure.

25. The method according to claim 1 wherein the human-machine interface is configured such that the set of total-utility-optimized parameters is specific to one or more of the machine, an application, and the user.

26. A system comprising:
    a human-machine interface; and
    a machine operatively coupled to the human-machine interface;
    the human-machine interface comprising at least one processor and associated memory, wherein the memory stores instructions executable by the at least one processor for performing operations comprising:
        receiving input from a user selecting preferred values of a set of user-tunable weights for determining a total utility function associated with the human-machine interface, wherein the total utility function includes a sum of a plurality of weighted utility functions, each weighted utility function depending on a respective utility factor, wherein each utility factor is associated with the utility of the human-machine interface as perceived by a user, wherein each weighted utility function is weighted according to a respective user-tunable weight, each user-tunable weight prescribing a relative importance of a respective utility factor to the total utility function, wherein the plurality of user-tunable weights associated with the total utility function define the set of user-tunable weights;
        determining a set of total-utility-optimized parameters based on the preferred values of the user-tunable weights and a reference dataset, the reference dataset providing, for each set of a plurality of different sets of user-tunable weights, a respective set of parameters that produces an optimized total utility function; and
        configuring the human-machine interface according to the set of total-utility-optimized parameters, such that the human-machine interface is indirectly configurable according to user input defining the preferred values of the user-tunable weights, in the absence of user input directly prescribing values for the plurality of parameters.

* * * * *